United States Patent [19]
Loos

[11] Patent Number: 5,800,481
[45] Date of Patent: Sep. 1, 1998

[54] THERMAL EXCITATION OF SENSORY RESONANCES

[76] Inventor: Hendricus G. Loos, 3019 Cresta Way, Laguna Beach, Calif. 92651

[21] Appl. No.: 580,346

[22] Filed: Dec. 28, 1995

[51] Int. Cl.$^6$ .................................................. A61F 2/00
[52] U.S. Cl. .................................................. 607/100
[58] Field of Search ............ 607/96, 98, 100–101, 607/107, 97–102, 115.3, 148, 152, 88–89; 128/741–743, 734; 600/26, 38; 606/2, 3, 13; 219/212; 165/46

[56] References Cited

U.S. PATENT DOCUMENTS

| 4,676,246 | 6/1987 | Korenaga | 128/399 |
|---|---|---|---|
| 5,315,994 | 5/1994 | Guibert et al. | 607/101 |
| 5,447,530 | 9/1995 | Guibert et al. | 607/107 |

FOREIGN PATENT DOCUMENTS

| 9409850 | 5/1994 | United Kingdom | 607/88 |
|---|---|---|---|

*Primary Examiner*—Jennifer Bahr
*Assistant Examiner*—Ryan Carter

[57] ABSTRACT

In man, autonomic and cortical resonances of the nervous system can be excited by inducing subliminal heat pulses in the skin by means of a resistive heat patch, laser, heat lamp, or microwave radiation, or through a slow air jet that carries a small periodic fluctuation in temperature. Deeply subliminal skin temperature oscillations of frequency near ½ Hz induced in a subject by any of these means cause sleepiness, drowziness, relaxation, a tonic smile, ptosis of the eyelids, a tense feeling, sudden loose stool, or sexual excitement, depending on the precise pulse frequency used. For certain higher frequencies, the induced subliminal skin temperature oscillations cause fractured thought and a slowing of certain cortical processes. The method and apparatus can be used by the general public as an aid to relaxation, sleep, or arousal, and clinically for the control and perhaps treatment of tremors, seizures, and emotional disorders. There is further application in the form of nonlethal weapons, involving a pulsed infrared laser or a pulsed microwave beam, tuned to a sensory resonance pulse frequency.

12 Claims, 7 Drawing Sheets

THERMAL EXCITATION OF SENSORY RESONANCES

BACKGROUND OF THE INVENTION

In man, the nervous system responds markedly to certain sensory signals in a narrow band of frequencies near ½ Hz; the response to the sensory signals includes sleepiness, drowsiness, relaxation, a tonic smile, ptosis of the eyelids, the feeling of a "knot" in the stomach, sudden loose stool, and sexual excitement, depending on the precise frequency used. The narrowness of the band of effective frequencies is suggestive of a resonance, and the phenomenon is therefore called "the ½ Hz sensory resonance". The resonance can be excited through the sense of balance, as we know from "rocking the baby" or relaxing in a rocking chair. But the resonance can also be excited by physical means other than motion, such as externally generated weak electric and magnetic fields, as discussed in the copending patent application Ser. Nos. 08/447394, [1], and 08/486918, [2]. The electric field excitation appears to involve stimulation of Ruffini endings in the skin [1], and the magnetic field excitation is believed to occur through stimulation of muscle spindles and the vestibular end organ [2]. All the receptors mentioned use frequency coding in their data transmission.

SUMMARY OF THE INVENTION

It has been shown in our laboratory that the induction of subliminal heat pulses with a frequency near ½ Hz in the human skin can cause sleepiness, drowsiness, relaxation, a tonic smile, ptosis of the eyelids, a tense feeling, sudden loose stool, and sexual excitement, depending on the precise pulse frequency used. The need for rather precisely tuned frequencies suggests that one is dealing with a resonance phenomenon. Since the resonances are excited through the senses and involve the autonomic nervous system, they are called "autonomic sensory resonances". Experiments have shown that, for the mentioned responses to occur, the amplitude of the skin temperature oscillations must fall in a rather restricted range, called the effective intensity window.

Further experimentation has shown the existence of resonances at higher frequencies. These resonances appear to involve cortical processes and are therefore called "cortical sensory resonances". A large resonance of this type has been found near 2.4 Hz, and smaller resonances have shown up near 2.2, 3.9, and 6.9 Hz. These resonances are detected by letting the subject repeatedly count backward from 100 to 70, while the frequency of the heat pulses is varied very slowly. The resonances show up as pronounced peaks in the graph of counting time versus heat pulse frequency. As is the case for autonomic sensory resonances, for the physiological effects to occur, the heat pulse amplitude must lie in a certain effective intensity window. The cortical sensory resonances cause a slowing of certain cortical processes. Furthermore, prolonged exposure to heat pulses near 2.4 Hz can cause mental states that may be characterized as "fractured thought". It takes considerable time for the responses to develop fully.

The heat pulses may be induced in the skin by conductive, convective, or radiative means. For conductive induction, the apparatus can be a battery-powered pulse generator that powers a small resistive heat patch placed on the skin of the subject. The heat patch employs either a resistive wire or a sheet of conductive polymer. Heat pulses suitable for excitation of autonomic or cortical sensory resonances are so weak as to be deeply subliminal.

Convective heat pulse induction may be achieved by an air jet which is heated in pulsed fashion. The jet is aimed at the face of the subject. The full array of physiological responses can be obtained even when the air velocity over the skin is imperceptibly small and the periodic fluctuations of the air temperature in the jet cause skin temperatures variations of subliminal magnitude.

Radiative induction may be achieved by a a pulsed heat lamp, a chopped heat lamp beam, a keyed laser beam, or by pulsed microwave radiation. The effective intensity window for excitation of the cortical sensory resonance near 2.4 Hz has been measured for the case of heat pulses induced in a large skin area by pulsed heat lamp radiation; the window has been found to extend from 0.8 to 3.0 mW/cm$^2$.

These discoveries open the way for influencing the nervous system of a subject by delivering weak heat pulses to the subject's skin. Devices for such purpose can be used by the general public as a sleeping aid, and as an aid for relaxation, control of anxiety and stage fright, or for facilitation of sexual arousal. Clinical use is seen for the control, and perhaps the treatment, of emotional disorders, tremors, and seizures.

Radiative heat pulse induction lends itself to application in non-lethal weapons for remotely exerting an influence on a subject's nervous system. This can be done covertly with a keyed infrared laser beam or with a pulsed microwave beam. In the latter case, high frequency is desirable since it results in small skin depths in human tissue, thereby minimizing the wasted heat generated in deeper lying tissue much below the cutaneous thermoreceptors.

DETAILED DESCRIPTION OF THE INVENTION

As mentioned in the Background Section, the excitations of the ½ Hz sensory resonance by rocking motion, weak external electric fields [1] and weak magnetic fields [2] all are believed to involve sensory receptors that use frequency coding for reporting information to the central nervous system. Since cutaneous thermoreceptors also use frequency coding [3,5], and skin temperature fluctuations may occur in rocking motions as a result of induced air currents, the question arises whether perhaps the ½ Hz sensory resonance can be excited also through cutaneous thermoreceptors. It has been found in our laboratory that this is indeed the case; when heat flux pulses of appropriate pulse frequency and intensity are delivered to the skin by a small resistive heat patch, the subject experiences autonomic nervous system responses that include sleepiness, drowsiness, relaxation, a relaxed soft feeling in the stomach, a tonic smile, ptosis of the eyelids, a "knot" in the stomach, sudden loose stool, and sexual excitement. The various responses occur at slightly different frequencies near ½ Hz. The appropriate frequency for each of these responses can be determined, either by the subject or by someone else in attendance, through manual frequency scanning, wherein the frequency of the heat pulses is manually adjusted, usually in monotonic fashion, in small steps until the desired response is obtained. From the observation that the various responses occur at slightly different frequencies it appears that the ½ Hz sensory resonance encompasses a multiplet of resonance frequencies, one for each particular autonomic response. When the heat pulses are first applied, the resonance frequencies are observed to undergo a downward drift, large at first, but diminishing in time. Eventually the frequency drift stops altogether, so that the resonance frequencies become steady. Crude preliminary experiments suggest that the multiplet of resonant frequencies drifts downward as a whole. Upon discontinuing the administration of heat pulses, the multiplet frequencies drift back up again, as can be seen during a brief resumption of the pulses. The frequencies for the various physiological responses depend somewhat on the state of the nervous system.

Of all the responses to the ½ Hz sensory resonance, ptosis of the eyelids stands out for distinctness, ease of detection and frequency sensitivity. When voluntary control of the eyelids is relinquished, the eyelid position is determined by the relative activities of the sympathetic and parasympathetic nervous systems. The heat pulse frequency for maximum ptosis is called the ptosis frequency; it can be found by manual frequency scanning. The ptosis frequency initially drifts downward, eventually settling at the steady ptosis frequency. The latter can be determined by manual tracking of the ptosis frequency, in which the frequency is manually adjusted such as to keep the ptosis maximum. At a fixed frequency slightly above the steady ptosis frequency the ptosis oscillates with a period of one or several minutes. Therefore, the steady ptosis frequency can also be determined by finding the frequency setting at which this oscillation ceases, and the ptosis remains strong and steady.

The intensity of the heat pulses delivered to the skin is an important parameter in the experiments; it has been noticed that the heat flux density must be very small, in fact deeply subliminal, for the mentioned responses to occur. This experimental result can be understood in terms of nuisance-guarding circuitry in the brain, that blocks nuisance signals from higher processing. Of course, these signals must exceed a certain strength for the guard circuits to be activated, and this signal strength determines the upper limit of a window of effective stimulus intensities. The lower limit of the window is determined by a signals which are only marginally able to excite the resonance. It has been found that a radiative power density of 0.6 mW/cm$^2$ from a heat lamp applied to a large part of the skin is suitable for exciting the ½ Hz resonance, evoking the whole array of autonomic responses mentioned for various frequencies near ½ Hz. At very low power densities it takes considerable time, up to half an hour, for physiological effects to develop. The frequency drift decreases with diminishing power density, but of course the slow development of responses makes frequency tracking difficult.

In extensive sleep experiments it has been found that pulse frequencies effective for inducing sleep are somewhat lower than the steady ptosis frequency. Before using a heat pulse device for the first time as a sleeping aid, it is recommended that a ptosis frequency is first determined by manual scanning. Then, starting with this frequency, the subject should adjust the tuning control every few minutes by a small downward frequency step, until sleep sets in. The final frequency setting should be written down in the morning, as it can be used as a fixed setting for the next session.

Heat pulses may be induced in the skin by conductive, convective, or radiative processes. In the first two cases, heat is delivered strictly to the surface of the skin, whereas with radiative induction there is heating by photon absorption in an extended layer of tissue. The intensity of the heat pulses induced in the skin by a device is defined here as the integral, taken over the line perpendicular to the skin, of the heat induced by the device per unit of time and per unit of volume in the skin and underlying tissue; it has the dimension of mW/cm$^2$. Note that the tissue under the skin is included in the integral; this is done in order to make the definition applicable to microwave radiation, which may have a skin depth [6] in excess of the thickness of the human skin. Thus, "induced in the skin" is here used as a brief form for "induced in the skin and underlying tissue". As formal cutoff for the integral a point may be used half way between the skin point considered and the diametrically opposed point on the skin which lies on the line of integration.

The array of autonomic responses elicited by induction of subliminal skin temperature oscillations is roughly the same as that achieved by application of weak electric or magnetic fields, as described respectively in copending U.S. patent application Ser. Nos. 08/447394, [1], and 08/486918, [2]. However, the dynamics of excitation and the guard circuitry involved cannot be quite the same for the three different stimulation modalities, since experiments with sleeping aid applications show that habituation of the nervous system to the stimulation can be thwarted to a large extent by switching stimulation modality after several nights of use.

Heat flux pulses, administered by a heat patch, have been applied successfully to the thighs, fingers, cheeks, neck, abdomen, and perinaeum. As compared with the electric and magnetic excitation, the thermal excitation of the ½ Hz sensory resonance has the advantage of a stricter localization of the stimulus. Although the electric or magnetic field can be localized to a considerable extent by the use of special electrodes or coils, the fields always have fringes that smear the boundary of the region of application. Such smearing is essentially absent in the thermal excitation with a heat patch. The strict localization of administration of heat flux pulses to the skin can be used, in research and perhaps clinically, for a novel kind of neurological testing of cutaneous thermoreceptors, their afferents, and the neural circuitry onto which the latter project. Furthermore, the stricter localization provides more options for diminishing habituation by shifting the application region.

Experiments have also shown the importance of the size of the skin area in which the heat pulses are induced. At an appropriate fixed value for the total heat pulse power, a greater physiological effect was obtained by increasing the skin area of application, so that the heat pulses are spread over a larger area.

Since the electric power dissipated in the resistive heat patch is quadratic in the driving voltage, the voltage pulses may as well be of single polarity, for the sake of efficiency. For square wave voltage pulses with 50% duty cycle, rising from 0 to V, the V/2 DC bias causes an initial average heating over periods, so that the long term temperature T of the cutaneous thermoreceptors oscillates around a slightly elevated temperature $T_{av}$. The receptors respond to the temperature oscillation by an oscillatory modulation of their firing frequency f. The receptor responsivity df/dT may depend on $T_{av}$.

Further experimentation in our laboratory has shown the existence of sensory resonances at higher frequency, albeit of a different nature than the ½ Hz resonance, because they appear to mainly involve the cortex rather than the autonomic system. These higher-frequency resonances manifest themselves as pronounced increases in the time needed by the subject to count backward from 100 to 70. Using radiative induction of heat pulses in the skin, a large resonance has been found near 2.4 Hz, and smaller resonances have shown up near 2.2 Hz, 3.9 Hz, and 6.9 Hz. Since counting backward through a sequence of numbers involves cortical processes, these resonances are here called cortical sensory resonances, in distinction with the multiplet of ½ Hz sensory resonances discussed earlier, which henceforth will be called autonomic sensory resonances. These names are not to be interpreted as implying that the resonances necessarily involve cortical and autonomic circuits in their resonance dynamics, but rather that the excitation of these resonances have respectively mainly cortical and autonomic consequences.

The cortical sensory resonances have been discovered only recently. Although there has been no time for investigating whether these resonances also can be excited by stimulations other than thermal, such as by electric or magnetic fields, this result is anticipated. In this regard, we report success in sleep experiments conducted over a period of three weeks, using stimulation of a nature different from heat pulses, at frequencies near 2.4 Hz. It has also been noticed that prolonged exposure to stimulation at these frequencies cause fractured thought and concentration difficulties. It is expected that such results may also be obtained from induction of heat pulses in the skin.

Although our pulsed heat induction experiments have not gone beyond frequencies of about 12 Hz, further cortical sensory resonances are expected to exist, perhaps up to 45 Hz. Collectively, the autonomic and cortical sensory resonances will here be called sensory resonances.

The discovery that in man certain sensory resonances can be excited by inducing heat pulses in the skin leads to a method and apparatus for artificially influencing the central nervous system of subjects. Certain devices based on this discovery may be used by the general public as a sleeping aid, or as an aid for relaxation, control of anxiety and stage fright, or for facilitation of sexual arousal.

Figure 1:
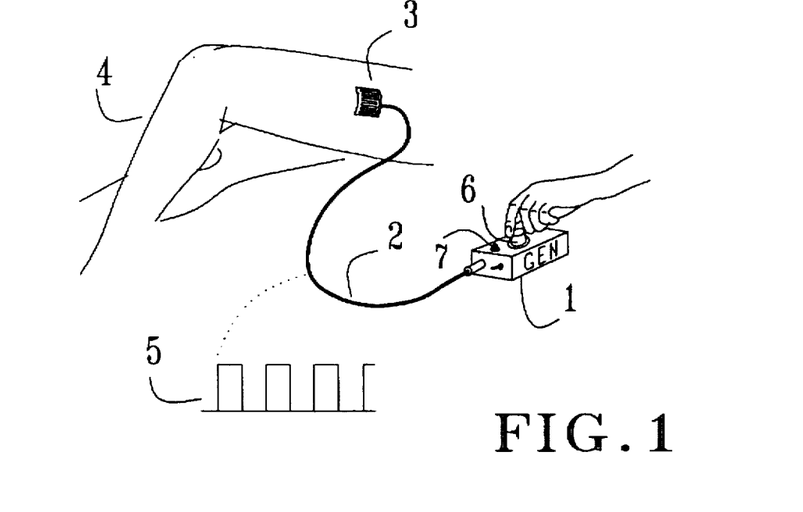
FIG. 1 shows a preferred embodiment in which weak heat pulses are induced conductively in the skin of a subject.

A preferred embodiment of the invention is shown in FIG. 1, where a voltage generator 1, labeled "GEN", is connected through a thin coaxial cable 2 to a small resistive heat patch 3, consisting of a resistance wire placed in a zig-zag pattern between two adhesive sheets of electrical insulator. The heat patch 3 is placed in physical contact with the subject 4 on a selected area of skin. The generator 1 produces current pulses 5 through the coaxial cable 2 and the resistive heat patch 3. The frequency of the voltage generator 1 can be manually adjusted with the tuning control 6, so that by manual scanning a pulse frequency can be found at which a sensory resonance is excited in the subject. The heat patch 3 may be secured to the skin with adhesive tape. Low pulse frequencies can be measured by monitoring the flashes of LED 7. The arrangement shown is particularly convenient for use as a sleeping aid. Instead of a resistance wire, a conductive polymer sheet may be used as the resistive element in the heat patch.

Figure 2:
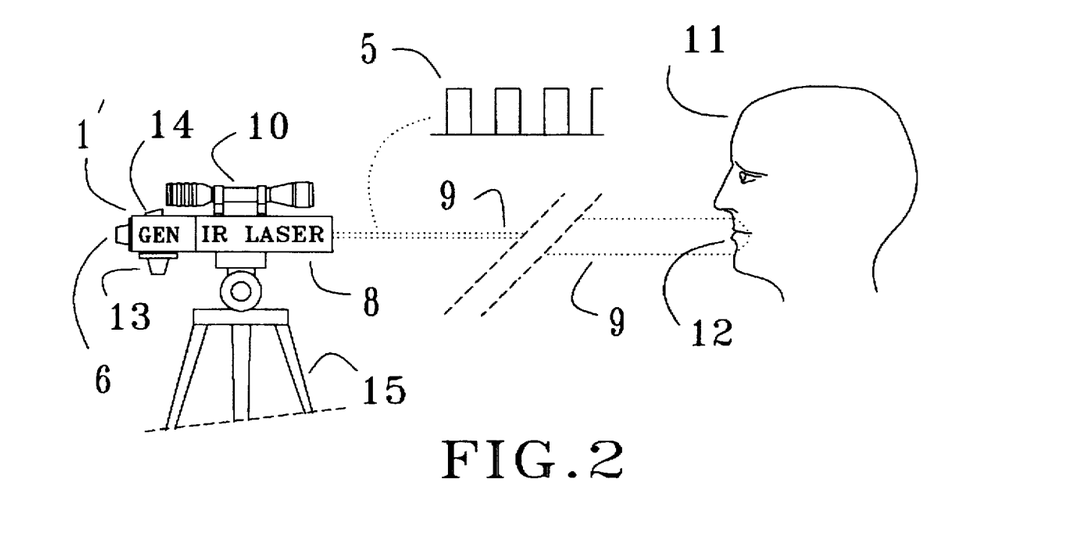
FIG. 2 shows an embodiment in which weak heat pulses are induced in the subject's skin by means of an infrared laser.

An embodiment in which heat pulses are induced in the skin of the subject in radiative manner is shown in FIG. 2, where generator 1, labeled "GEN", produces voltage pulses with a frequency that can be adjusted with the tuning control 6. The voltage pulses drive an infrared cw laser diode which, together with collimating optics, is shown as assembly 8 labeled "IR LASER". The laser assembly 8 produces an invisible infrared laser beam 9 which is keyed on and off according to the pattern 5. By using the telescopic sight 10, the laser beam 9 can be aimed at a distant subject 11, preferably at the lips 12. The strength of the voltage pulses that drive the laser laser is adjusted by the amplitude control 13 such that the radiative power density at the subject's skin lies in the effective intensity window for excitation of sensory resonances. When the tuning control 6 is then set to an appropriate frequency, the frequency modulation signal in the afferents from the cutaneous thermoreceptors will excite in the subject a sensory resonance. The pulse frequency may be read from the display 14. For frequencies near ½ Hz, excitation of the subject's autonomic sensory resonance will cause sleepiness, woosiness, relaxation, ptosis of the eyelids, arousal, sudden loose stool or sexual excitement, depending on the precise frequency used. For higher frequencies in the range from 1 to 45 Hz, excitation of cortical sensory resonances will cause a slowing of certain cortical processes and, after prolonged exposure, fractured thought; some secondary autonomic responses may occur as well. A complex wave may be used for laser keying, such that autonomic and cortical sensory resonances are excited together. The apparatus may be used as a non-lethal weapon for covert operations, in which the nervous system of a selected subject is influenced in a chosen manner, from a considerable distance. In practice, the range of the device is limited only by line-of-sight and visibility restrictions. The assembly consisting of the generator 1, the laser 8, and the telescopic sight 10 can be mounted on a tripod 15, the upper part of which is shown in FIG. 2. Instead of a cw laser, a pulsed laser may be used, and the pulses are then keyed on and off with the square wave produced by the generator 1. In practice, the temperature fluctuations due to the individual laser pulses are smoothed out by diffusion on their way through the skin so that the cutaneous thermoreceptor temperature essentially oscillates only with the keying frequency. Instead of a manual tuning control, the pulse train that keyes the laser can be controlled automatically by a programmed processor such as the Basic Stamp [4], in a manner known to those skilled in the art.

Experiments have been conducted at our laboratory with a 5 mW laser beam produced by a 670 nm cw laser diode. The 1 cm diameter visible laser beam was aimed at a subject's lips. Keying the laser on and off with frequencies near ½ Hz and a 50% duty cycle caused the same array of physiological responses as found with the heat patch application. Similar results were obtained with the laser aimed at the upper part of the right foot of the subject.

Figure 3:
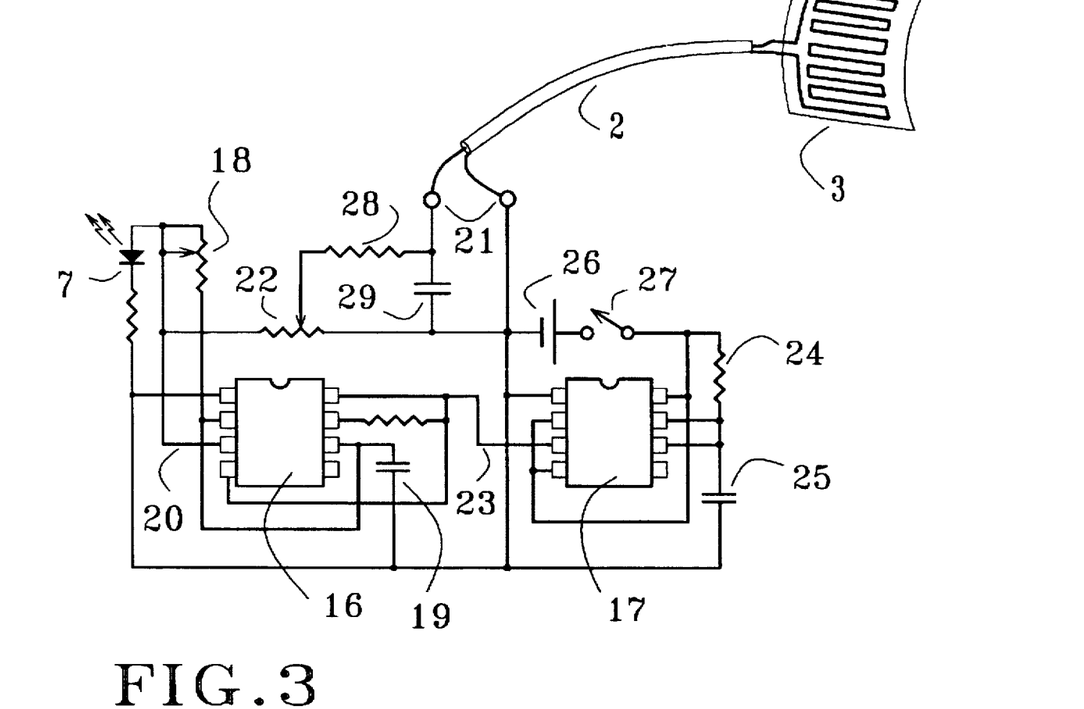
FIG. 3 is a circuit diagram for a pulse generator suitable for use in the arrangement of FIG. 1.

A simple pulse generator for use with a resistive heat patch is shown in FIG. 3. The battery-powered generator is built around two RC timers 16 and 17. Timer 16 (Intersil ICM7555) is hooked up for astable operation; it produces a square wave voltage with a frequency determined by potentiometer 18 and capacitor 19. The square wave voltage at output 20 drives the LED 7, and appears at one of the output terminals 21, after voltage division by potentiometer 22. The other output terminal is connected to the negative supply. The output terminals 21 are connected, via a thin coaxial cable 2, to the resistive heat patch 3. Automatic shutoff of the voltage that powers the timer 16 at point 23 is provided by a second timer 17 (Intersil ICM7555), hooked up for monostable operation. Shutoff occurs after a time interval determined by resistor 24 and capacitor 25. Timer 17 is powered by a 3 volt battery 26, controlled by a switch 27. Rounding of the square wave is done by an RC circuit consisting of a resistor 28 and capacitor 29.

Figure 4:
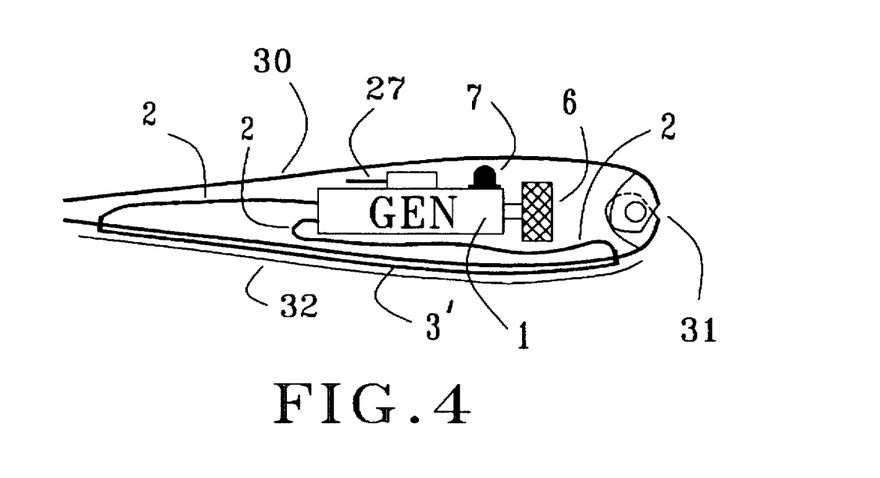
FIG. 4 shows a packaging of the pulse generator and heat patch in a single enclosure.

A compact packaging of the device of FIG. 3 is shown in FIG. 4, where all circuit parts and the heat patch are confined to a small clam-type enclosure, such as an eye shadow box 30 with hinge 31. Shown are the generator 1, labeled "GEN", with tuning control 6, LED 7, and power switch 27. The generator provides current pulses through a thin conductive polymer sheet 3', via connecting wires 2. The conductive polymer sheet 3' is covered by an electrically insulating film 32, which for purposes of semantic definition is here considered as part of the boundary of the enclosure.

Figure 5:
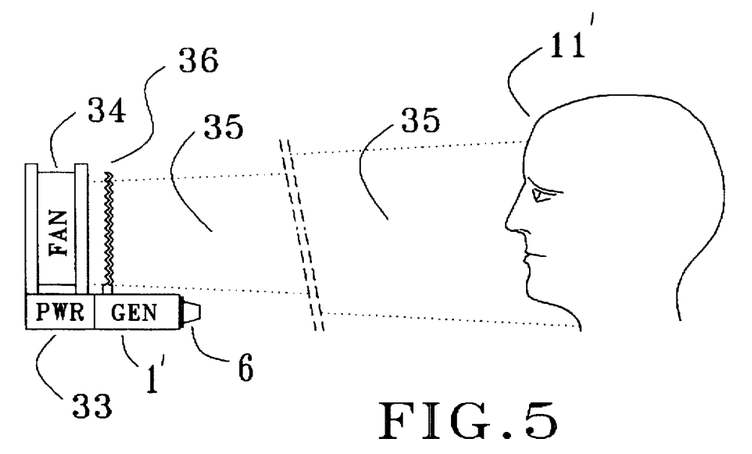
FIG. 5 depicts an embodiment in which weak heat pulses are convectively induced in the subject's skin by means of an air jet.

An embodiment with convective heat pulse induction is depicted in FIG. 5. Shown are a power supply 33, labeled as "PWR", that provides power for a fan 34, labeled as "FAN", which produces a jet 35 in the surrounding air. The jet is made to pass through a grid 36 of resistor wires that are driven by voltage pulses from a generator 1', labeled as "GEN", with pulse frequency tuning control 6. The voltage pulses cause the resistor wires to be heated in a pulsed manner, with the result that the air jet 35 exhibits a wave-like temperature pattern, which is convected downstream with the jet motion. Hence, a subject 11' whose face is exposed to the jet will undergo a pulsating heat flux to the skin. Experiments in our laboratory with this type device have induced in the exposed subject the array of autonomic responses mentioned above. In these experiments, the flow of air over the subject's face was too slow to be sensed, and the rythmic temperature fluctuations induced in the skin were imperceptible as well. The apparatus is thus suitable for influencing a subject's nervous system in a covert manner.

Figure 6:
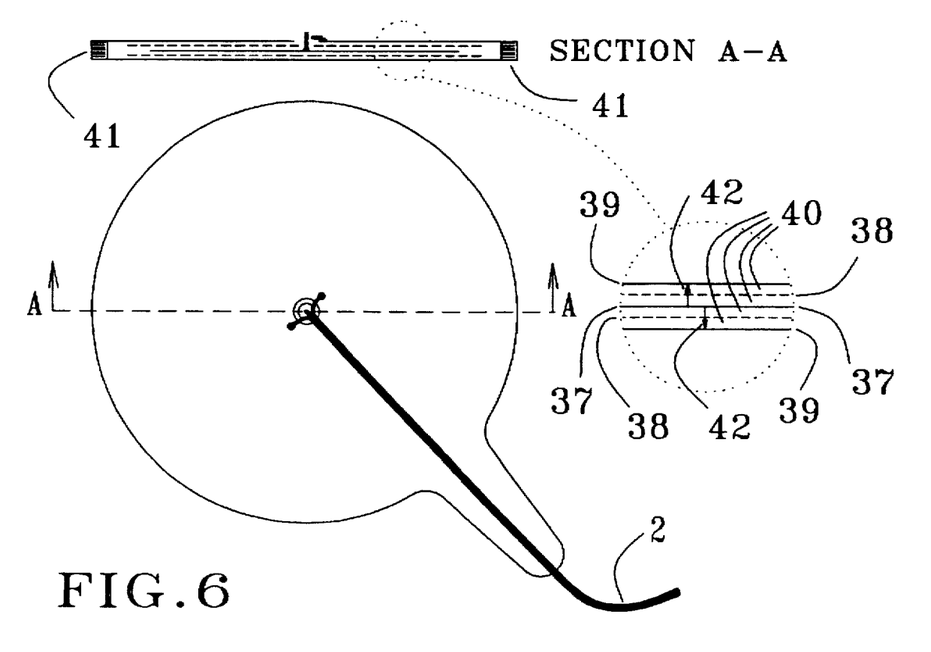
FIG. 6 shows a heat patch designed to minimize the emanated electromagnetic field.

A resistive heat patch may generate electric and magnetic fields as a side effect. Since such fields may contribute to the excitation of sensory resonances [1,2], they are undesirable in certain situations, such as in research on purely thermal excitation. If a heat patch is to be used in such situations, it must be shielded so that the emanating electric and magnetic fields are reduced to negligible magnitude. A design for such a shielded heat patch is depicted schematically in FIG. 6, which shows a sandwich consisting of an inner electrode 37 in the form of a plane metal foil, mounted between two thin sheets 38 of conductive polymer, covered by the outer electrodes 39 in the form of plane metal foils. An electrically conductive epoxy is used in the spaces 40 to secure electric contact between the electrodes and the conductive polymer. The inner electrode 37 is electrically connected to the center conductor of the coaxial feed cable 2, and the outer electrodes 39 are connected to the braid. The connections are made in the center of the heat patch, in order to obtain axisymmetry of the currents through the electrodes. The two outer electrodes are connected together by a conductive epoxy joint 41. During operation of the heat patch, the inner electrode 37 is given a voltage with respect to the outer electrodes 39, but since the latter form an enveloping shield, no electric field emanates from the assembly. The electric currents 42 that flow from the inner electrode to the outer electrodes are distributed throughout the conductive polymer; the magnetic fields induced by these currents of opposite directions essentially cancel outside the device, if the sandwich is very thin. The electric currents flowing along the electrodes also have opposing directions and the same planar pattern, if the sandwich has symmetry in the normal direction; the magnetic field of these currents then also essentially vanishes if the sandwich is very thin. Sandwiches as thin as 0.5 mm can easily be constructed. The outer electrode that is not to be in physical contact with the skin can be covered with several layers of insulating tape, in order to increase the stiffness of the assembly, and to decrease the convective heat loss to the surrounding air. The driving circuit should be such that the outer electrodes remain at ground potential, and then no electric insulation needs to be used between the heat patch and the skin of the subject.

Figure 7:
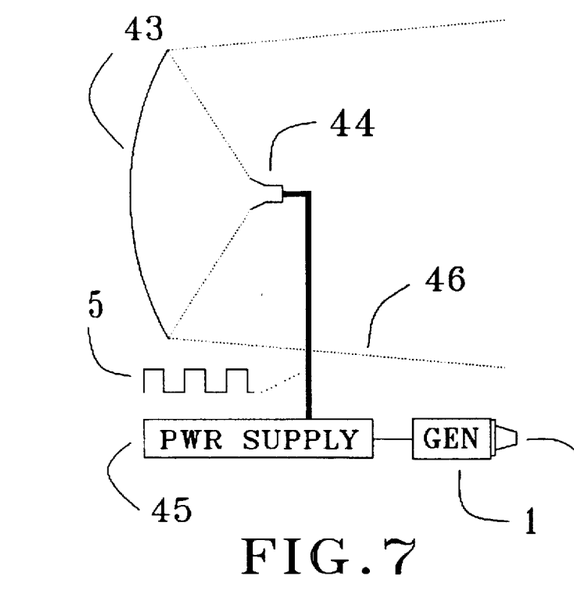
FIG. 7 shows schematically an embodiment in which a beam of pulsed microwave radiation is produced for the purpose of thermal excitation of sensory resonances in exposed subjects.

An embodiment in which the heat pulses are induced by microwave radiation is depicted schematically in FIG. 7. Shown are a microwave dish 43 illuminated by a horn 44 driven by a power supply 45, labeled "PWR SUPPLY". A pulse generator 1, labeled "GEN", is connected to the power supply such that the microwave voltage supplied to the horn 44 is modulated by a square wave 5. The frequency of the square wave 5 can be adjusted by the tuning control 6. Subjects within the microwave beam 46 will undergo a weak pulsed heating of an outer layer of their bodies, the thickness of which is about the skin depth [6] for the microwave frequency used; for a microwave frequency of 250 GHz, the skin depth in human tissue is about 1 mm. In a certain window of microwave power densities, the induced temperature oscillation of cutaneous thermoreceptors will cause excitation of sensory resonances at appropriate pulse frequencies. The device can be used as a nonlethal beam weapon for remotely influencing the nervous system of foes.

Figure 8:
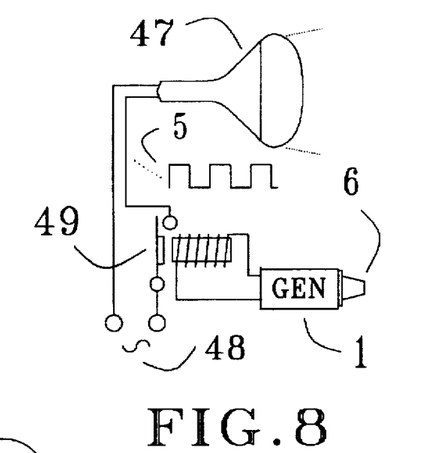
FIG. 8 shows a source of pulsed radiation in the form of heat lamp that is periodically switched on and off by a solenoid.

A device which produces radiative power pulses for therapeutic purposes is shown in FIG. 8. A heat lamp 47 is powered by AC current 48 via a relay 49 which is energized by voltage pulses produced by the generator 1, labeled "GEN". As a result, the heat lamp is pulsed on and off according to the square wave 5. The frequency of the pulses 5 can be varied through the frequency control 6. For excitation of sensory resonances, the heat lamp is aimed at a selected portion of the subject's skin. The subject's eyes must be shielded from the radiation.

Figure 9:
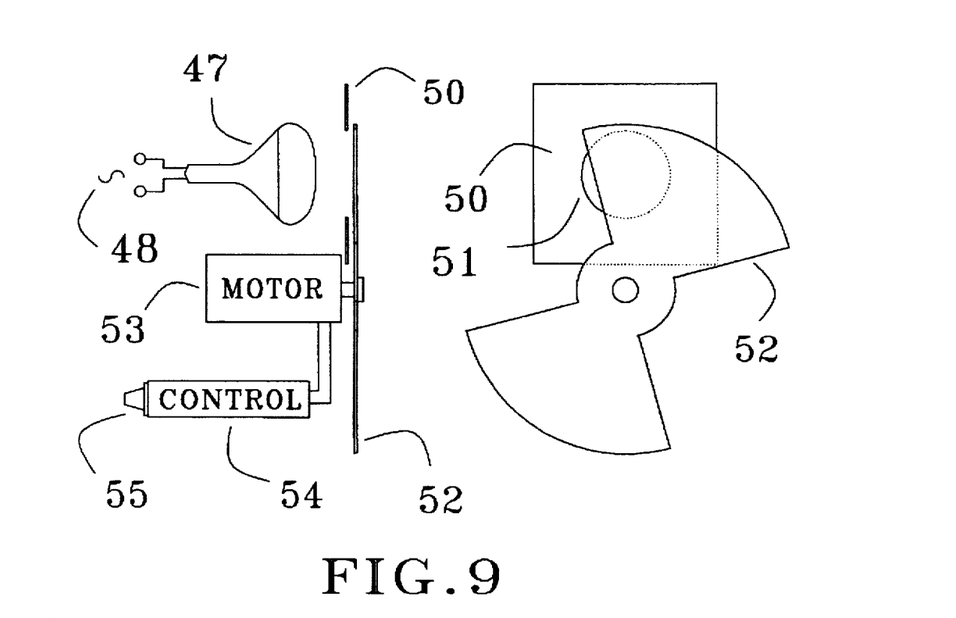
FIG. 9 shows an embodiment in which pulsed radiation is produced by chopping a beam of radiation from a heat lamp.

Periodic radiative flux may also be obtained by chopping a steady radiative beam. FIG. 9 shows such a device wherein a heat lamp 47 is powered by AC current 48. A baffle 50 with hole 51 is arranged such as to confine the radiation to a beam, and the latter is interrupted periodically by the chopper 52 which is rotated steadily by the electric motor 53, labeled "MOTOR". The speed of the motor is controlled by the controller 54 labeled "CONTROL". The pulse frequency of the beam can be set through the manual tuning control 55. The pulsed beam is to be aimed at a selected area of a subject's skin, for the purpose of exciting sensory resonances. The beam can also be chopped by an array of parallel rotating strips in a louver arrangement; this approach affords a more compact device.

Figure 10:
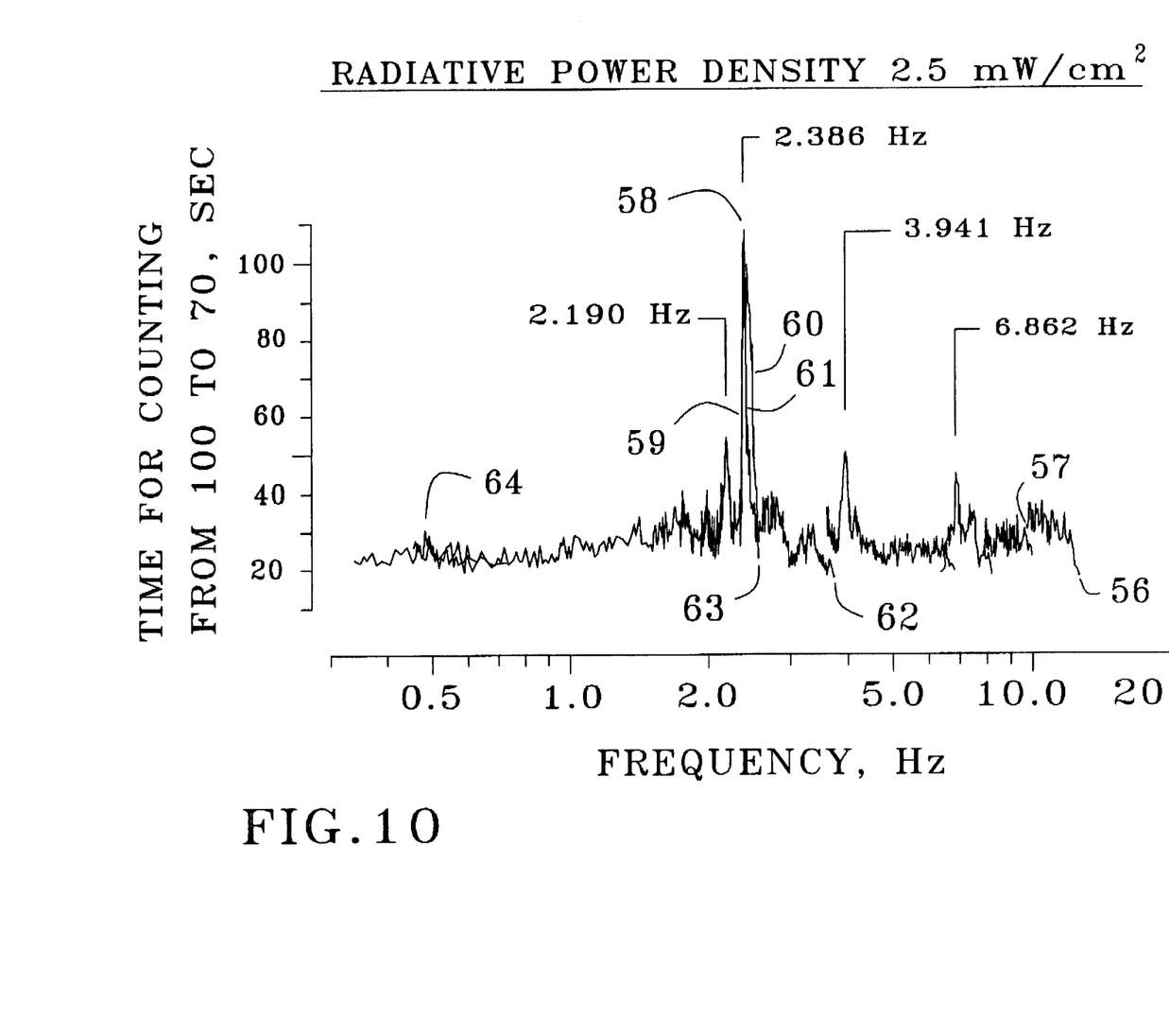
FIG. 10 shows cortical sensory resonances in a graph of a subject's 100-70 counting time versus the frequency of radiatively induced heat pulses.

Presently, the experiments which show the existence of cortical sensory resonances are described. The blinking heat lamp of FIG. 8 was used, but generator 1 was replaced by a computer running a program which causes a computer port to produce voltage pulses, that are used to drive the solenoid via an interface. The computer slowly made small downward adjustments in the pulse frequency. The heat lamp was aimed at the subject who was unclothed, in order to expose as much skin to the radiative heat as possible. The subject's eyes were closed and shielded from the radiation. A quantitative measurement made by the subject comprises repeatedly counting backward from 100 to 70 as rapidly as possible, and recording each counting time. The counting was done with the "silent voice" which is accompanied by a sensation of slight stress in the vocal cords, instead of by mere thinking of the numbers, which does not produce such sensation. The distinction between these two modes of silent counting is important, since the former is much more responsive to the stimulus than the latter. FIG. 10 shows a graph of the counting time versus radiative heat pulse frequency, for an experiment in which the subject's skin was exposed to heat radiation which, at the point of the skin closest to the heat lamp had a peak power density of 2.5 mW/cm$^2$. The pulse frequency was changed very slowly, since at any one frequency considerable time is needed for the development of a full response to the heat pulses. Since a large frequency range had to be covered, the experiment was arranged over several days as a set of separate runs of sensible duration; the starting point 56 and end point 57 of one such run at the extreme right in the graph are indicated. The graph is therefore a cumulative plot of individual runs, some of which have an overlap in frequency. In all runs the frequency was slowly decreased, in a leftward direction along the graph. A large peak 58 is seen near the pulse frequency of 2.4 Hz, with smaller peaks near 2.2 Hz, 3.9 Hz, and 6.9 Hz. The large peak 58 shows up in two different runs, with the trailing edges of the peaks coinciding as marked by 59, and the leading edges 60 and 61 somewhat separated. Near ½ Hz, the graph shows only an insignificant peak 64.

Figure 11:
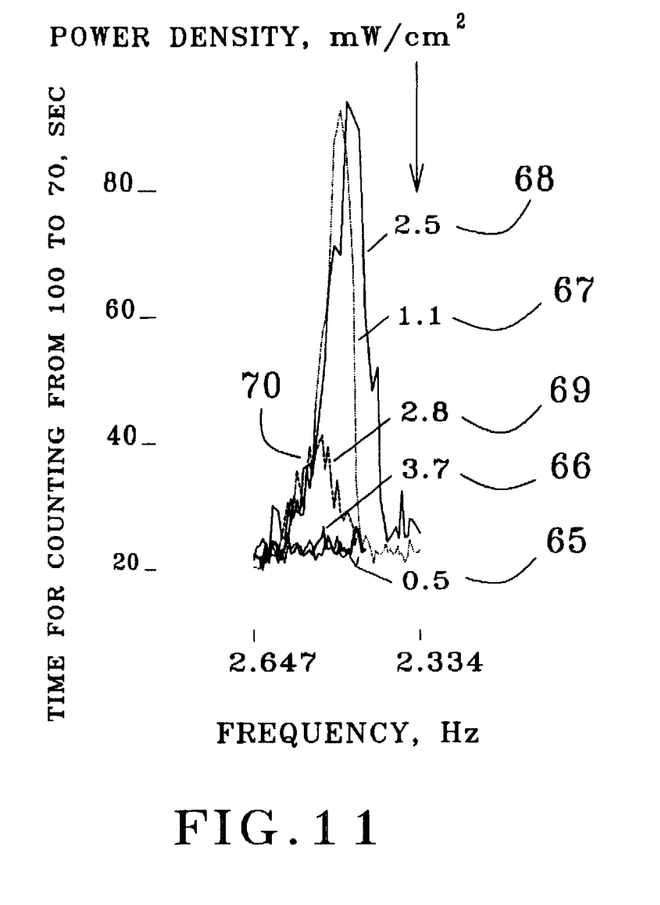
FIG. 11 shows excitation of the cortical sensory resonance near 2.4 Hz, for different levels of power density at the subject's skin, and reveals the effective intensity window.

As discussed, the intensity of the stimulus must fall in a certain effective intensity window, in order that the mentioned physiological effects occur. The quantitative subjective measurement of counting time discussed above affords an opportunity for investigating the effective intensity window. This was done by making experiment runs across the peak 58 of FIG. 10, using different values for the radiative power density. The results of these runs are shown in FIG. 11, where graphs of the counting time versus frequency are shown for radiative power densities ranging from 0.5 to 3.7 mW/cm$^2$, for frequencies in the range from 2.334 Hz to 2.647 Hz. The effective window is clearly seen, since an appreciable peak is absent in graph 65 for the low power density of 0.5 mW/cm$^2$ and also in graph 66 for the high power density of 3.7 mW/cm$^2$, whereas large peaks occur for graphs 67 and 68, respectively for intermediate power densities of 1.1 and 2.5 mW/cm$^2$. The decline of response near the upper end of the intensity window is evident in graph 69 for a power density of 2.8 mW/cm$^2$, which has a low peak. Note that the leading edges of the peaks essentially coincide, as indicated by 70.

Figure 12:
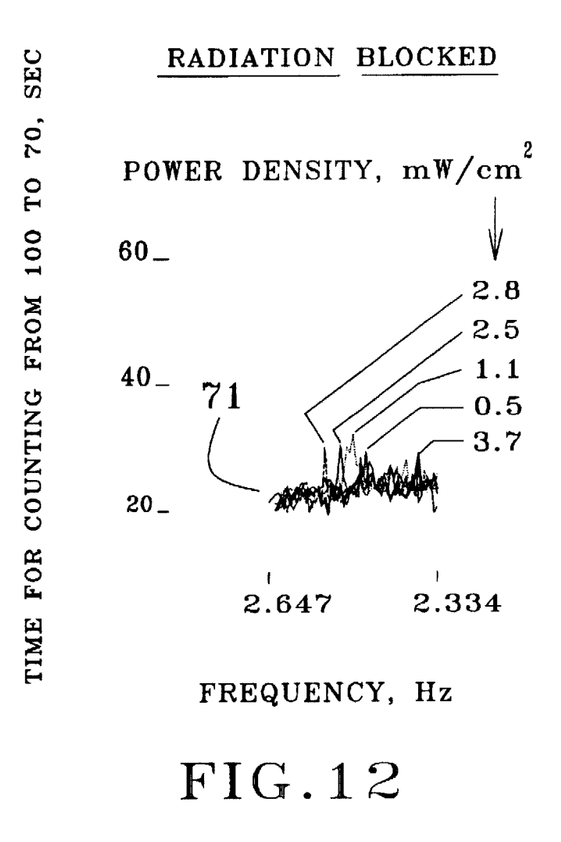
FIG. 12 shows the effect on the subject of the stray 60 Hz electromagnetic field emanating from the heat lamp.

There needs to be concern that the electric and magnetic fields which emanate from the pulsed heat lamp and its driving circuitry may contribute or perhaps dominate the measured physiological response. Therefore, the experiments of FIG. 11 were repeated while the radiation from the heat lamp was blocked from striking the skin of the subject. In all other respects the experiment was the same, and in particular, the electromagnetic fields emanating from the device and exposing the subject were the same. The results of the experiment with blocked radiation are shown in FIG. 12, where for all power densities shown, the graphs 71 are without significant peaks. It follows that the peaks of FIG. 11, for 1.1, 2.5, and 2.8 mW/cm$^2$, are not due to electromagnetic fields, but are indeed caused by the pulses of radiation impinging on the subject's skin.

Figure 13:
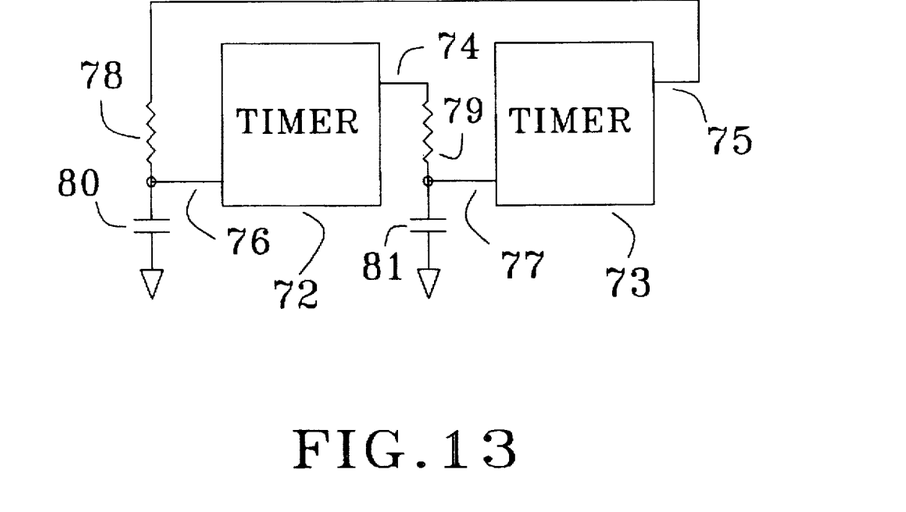
FIG. 13 shows schematically two cross-coupled timers which produce a chaotic output.

So far, the heat pulses discussed were periodic. However, for the purpose of thwarting habituation to the stimulation, irregular features may be introduced in the pulse train, such as short-term variations of frequency of a chaotic or stochastic nature. Such chaotic or stochastic heat pulses can cause excitation of a sensory resonance, provided that the dominant frequency of the pulses is close to the appropriate sensory resonance frequency. The dominant frequency of pulses is defined here as the frequency at which the norm of the Fourier transform of the temperature pulse train attains its maximum. If the maximum is not unique, the lowest frequency in the set of maxima is formally taken as the dominant frequency. For the purposes of this invention, the dominant frequency needs to lie in the range 0.1 to 45 Hz, in order to include the known resonances, and to allow for the possibility that further resonances exist below ½ Hz and above 12 Hz. A chaotic square wave can be generated in a simple manner by cross coupling of two timers. FIG. 13 shows such a hookup, where timers 72 and 73, each labeled "TIMER", have their output pins 74 and 75 connected crosswise to each other's control voltage pins 76 and 77, via resistors 78 and 79. The control voltage pins 76 and 75 have capacitors 80 and 81 to ground. If the timers are hooked up for astable operation with slightly different frequencies, and appropriate values are chosen for the coupling resistors and capacitors, the output of either timer is a chaotic square wave with an oval attractor. Example circuit parameters are: $R_{78}$=440 KΩ, $R_{79}$=700 KΩ, $C_{80}$=4.7 μF, $C_{81}$=1.0 μF, with $(RC)_{72}$=0.83 s and $(RC)_{73}$=1.1 s. For these parameters, the output 74 of timer 72 is a chaotic square wave with a power spectrum that has large peaks near 0.40 Hz and 0.62 Hz. The chaotic wave is suitable for the excitation of the ½ Hz sensory resonance.

Figure 14:
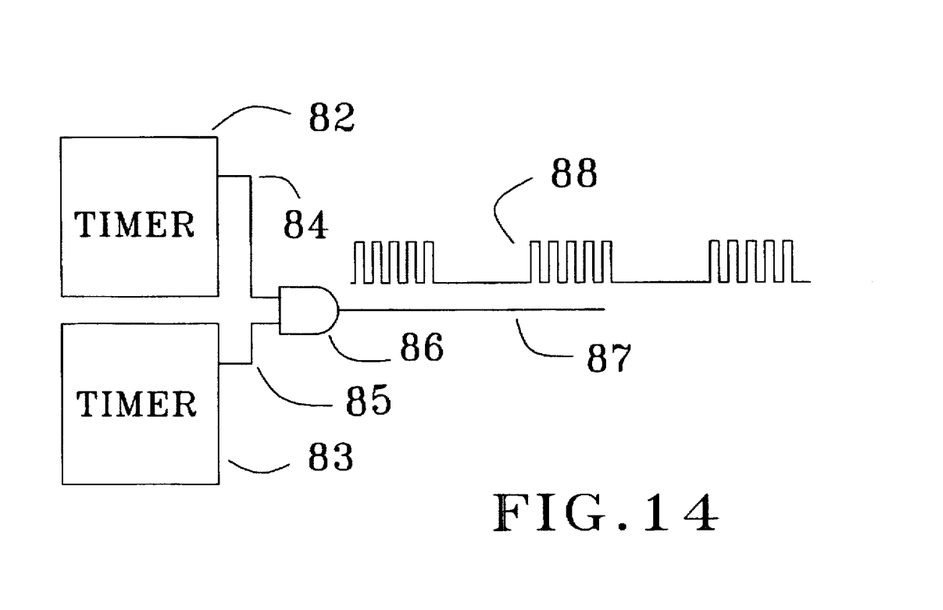
FIG. 14 shows schematically the hookup of two timers such as to produce a square wave of frequency $f_1$, amplitude-modulated by a square wave of frequency $f_2$.

As mentioned before, a complex wave may be used for the excitation of sensory resonances. Although this possibility was mentioned in regard to the keyed laser of FIG. 2, it can also be used with several other heat pulse induction devices, such as the resistive heat patch of FIG. 1, the air jet with pulsed temperature of FIG. 5, the pulsed microwave radiator of FIG. 7, and the pulsed heat lamp of FIG. 8. A simple generator of a complex wave, suitable for the joint excitation of a ½ Hz autonomic resonance and the 2.4 Hz cortical resonance, is shown in FIG. 14. Timers 82 and 83 are arranged to produce square waves of frequencies $f_1$ and $f_2$ respectively, where $f_1$ is near 2.4 Hz, and $f_2$ is near 0.5 Hz. The outputs 84 and 85 of the timers are connected to the inputs of an AND gate 86. The output 87 of the AND gate produces a square wave of frequency $f_1$, amplitude modulated with a square wave of frequency $f_2$, as indicated by 88.

Complex, chaotic, or stochastic waves can be generated easily by a programmed processor, such as the Basic Stamp [4], and programs can be tailored towards thwarting habituation to the stimulus.

As noted before, the ptosis frequency initially drifts downward towards the steady ptosis frequency. The characteristic time for this frequency drift depends on the stimulus intensity, but is at least several minutes. This suggests that the resonance is modulated by a process, the rate of which is controlled by bulk substance release or uptake and perhaps diffusion; candidates for the substance involved are neurotransmitters, second messengers, and hormones. The process whereby the ptosis frequency is influenced by the bulk substance release, uptake, or diffusion is here called chemical modulation of the resonance. It is expected that the substance concentration perturbations have other, "extended" physiological effects as well. For instance, pathological oscillatory activity of neural circuits, such as tremors and seizures, is influenced by the chemical milieu of the circuits. So are emotional disorders such as depression, mania, anxiety, and phobia. Hence, the manipulation of the autonomic nervous system by means of heat pulses induced in the skin may afford, through extended chemical modulation, some measure of control of these disorders, and of tremors and seizures as well. It is postulated here that such control is possible. The control may also provide a treatment of some of the disorders, through conditioning and other plastic modifications of neural circuits.

The invention may also be used to help prevent epileptic seizures by switching on the thermal stimulation when a precursor or aura is felt by the patient. A somewhat similar use is seen for the prevention of panic attacks.

The invention may be further be used for controlling tremors by upsetting pertinent pathological oscillations through the activity of neural circuits partaking in a suitable sensory resonance.

The cortical sensory resonance frequencies have not been observed to drift. However, the physiological response to the stimulation builds very slowly. This has been shown in an experiment using the pulsed heat lamp of FIG. 8, where the subject is nude, with the eyes closed and shielded from the radiation. The radiant power density was 1.1 mW/cm$^2$ reckoned at the point of the subject's skin closest to the heat lamp center, and the pulse frequency was fixed at 2.386 Hz, at the peak 58 in FIG. 10. In the experiment, the time needed for counting backward from 100 to 70 was seen to rise slowly from about 20 s to about 60 s in 13.5 minutes; the counting time increased further to about 90 s in another 14 minutes, whereafter it stayed roughly at 90 s for the 32.5 minute remainder of the experiment. A similar experiment with power density of 0.5 mW/cm$^2$ showed a rather flat response, ranging from 20 to 29 s over the 20 minute duration of the experiment. The slow development of the physiological response may perhaps explain the lag, in FIG. 10, of the leading edge 61 of the peak 58 behind the leading edge 60 of a run that had been going for a longer time; the starting points of the former and latter runs are indicated respectively by 63 and 62. From point 63 to point 61 the elapsed time was 23 min, compared with 112 minutes elapsed from point 62 to point 60. It is not known whether the slow development of the physiological response is due to the slow growth in amplitude of oscillations of resonant neural circuits, or caused by the slow increase of perturbations in substance concentrations that develop as a result of the resonance. Applications of cortical sensory resonances are envisioned to include sleeping aids and sleep therapy, and the control and treatment of emotional disorders, tremors, and seizures.

For purposes of design and research, the transfer function from oscillating power density incident on the skin to thermoreceptor temperature oscillation needs to be known. The transfer function is needed for the three modes of pulsed heat induction: conductive, convective, and radiative.

For conductive pulsed heat transfer, the calculation of the transfer function proceeds as follows. A spatially uniform harmonically varying thermal flux density P* sin ωt delivered to the outer skin surface causes at depth z below the outer skin surface a temperature fluctuation $$T(z) = \left( \frac{P^* \sqrt{2}}{c\rho\delta\omega} \right) e^{-z/\delta} \sin(\omega t - z/\delta - \pi/4), \quad (1)$$

where c is the specific heat and ρ the mass density of the tissue, and δ is a diffusion length given by $$\delta = \sqrt{(2k/\omega)}, \quad (2)$$

k being the thermal diffusivity of the tissue. Eq. (1) is the one-dimensional solution of the diffusion equation for a semi-infinite homogeneous slab, with a prescribed uniform value for ∂T/∂z at the surface, determined by the delivered thermal flux. It follows from Eq. (1) that at depth z the temperature oscillation has an amplitude $$T^*(z) = \left( \frac{P^* \sqrt{2}}{c\rho\omega\delta} \right) e^{-z/\delta}. \quad (3)$$

Eq. (3) shows that the heat diffusion from the skin surface z=0 to the depth z of the thermoreceptors acts as a low pass filter because of the factor ωδ in the denominator and the exponential factor, considering how the diffusion length δ depends on frequency. This low pass filter effect is here called diffusional filtering. For numerical calculations one must know the depth z of the thermoreceptors, as well as the diffusivity k in the skin. There are two types of thermoreceptors: warm receptors and cold receptors. According to Hensel [5], in man thermoreceptors lie at an average depth of 0.3 to 0.6 mm for warm, and 0.15 to 0.17 mm for cold receptors. Hensel [5] has also measured the thermal diffusivity k in man in the forearm skin, and reports k=0.0006 cm$^2$/s at 0.45 mm depth, and 0.001 cm$^2$/s at 0.90 mm. In human skin, cold receptors are much more dense than warm receptors [5]. As a consequence of diffusional filtering, the higher harmonics of the applied pulse wave form are severely attenuated at the level of the thermoreceptors. This explains the experimental finding that for thermal excitation of the ½ Hz autonomic sensory resonance a square wave pulse can be used without experiencing the harsh sensation that occurs for magnetic excitation [2]. When Eq. (3) is to be used for calculating the thermoreceptor temperature oscillation amplitude that results from a given sinusoidal heat stimulation, the heat capacity c and mass density ρ of the skin tissue must be known. Values of these parameters given by Van Bladel [8] result in cρ=3.7 J/°cm$^3$ for muscle, and cρ=3.6 J/°cm$^3$ for blood.

When calculating the receptor temperature oscillation amplitude that results from a given oscillating electric power dissipation in the heat patch, one must account for the power needed for heating the patch itself. The calculation is simple for the case of a thin patch that consists of materials with large thermal conductivity; then, throughout the patch the temperature is essentially uniform and equal to T(0) given by Eq. (1). The total oscillatory electric power density dissipated in the heat patch is then $$P^*_e = P^* \sin\omega t + C_p \partial T(0)/\partial T = P^* \sin\omega t + (C_p \sqrt{2}/c\rho\delta)\cos(\omega t - \pi/4), \quad (4)$$

where $C_p$ is the heat capacity of the heat patch per unit of surface area. In Eq. (4), the term P* sin ωt is the density of the power transmitted across the interface z=0, from the heat patch to the skin, per unit of area. Use has been made of Eq. (1) for the calculation of the time derivative of the skin surface temperature. Accounting for the phase difference of the two terms on the right hand side of Eq. (4), the total oscillatory electric power dissipated in the heat patch per unit of area is found to have an amplitude $$P^*_e = P^* \sqrt{(1 + 2C_p^2/c^2\rho^2\delta^2 + 2C_p/c\rho\delta)} \ , \tag{5}$$

where the cosine law has been used in the composition of two vectors that include an angle $\pi/4$. Eqs. (3) and (5) give $$P^*_e = \omega T^*(z, \omega) e^{z/\delta} \sqrt{(c^2\rho^2\delta^2/2 + C_p^2 + C_p c\rho\delta)} \ , \tag{6}$$

so that at depth z below the skin surface the temperature oscillation amplitude can be calculated from the amplitude of the electric power density dissipated in the heat patch by using an effective heat capacity per unit of area $$C_{ef}(z, \omega) = e^{z/\delta} \sqrt{(c^2\rho^2\delta^2/2 + C_p^2 + C_p c\rho\delta)} \ . \tag{7}$$

$C_p$, the patch heat capacity per unit of patch area, can be measured by taping a small thermistor to the patch surface, and covering the assembly with thermal insulation tape. A step function voltage is applied to the heat patch, and the thermistor temperature is measured at selected times. From these data and the thermal response of the thermistor itself, $C_p$ can then be determined. A typical value for $C_p$ is 0.1 J/°cm$^2$.

When the heat pulses are induced in the skin convectively, the skin is directly warmed and cooled by the surrounding air flow. Standard convective heat transfer theory [9] may be used to calculate the skin temperature oscillation that results from a given temperature fluctuation in the air jet. The temperature fluctuation at depth z of the thermoreceptors can then be calculated from Eq. (1), by eliminating the factor in front of the exponential by using the known skin temperature T(0).

When the heat pulses are induced radiatively, heat is generated in the skin by absorption of photons throughout a layer of some thickness, and the relation (1) does not hold. Instead, one must use the inhomogeneous diffusion equation $$\partial T/\partial t - k\partial^2 T/\partial z^2 = p/(c\rho), \tag{8}$$

where p is the density of the heat generated by photon absorption per unit of time t at depth z. For the model in which a semi-infinite uniform absorbing slab is illuminated by a harmonically varying flux of monochromatic photons, the rate of deposited radiative heat per unit of area may be taken as $$p = P^* \alpha \cos \omega t \ e^{-\alpha z}, \tag{9}$$

where $\alpha$ is the effective absorption coefficient of the photons and $P^*$ is the oscillation amplitude of the total radiative power absorbed by the slab, per unit of surface area. The effective absorption coefficient $\alpha$ must include the effect of multiple scattering of photons in the tissue. A solution of Eqs. (8) and (9) is $$T = \frac{\alpha P^*}{c\rho\omega(1+\xi^2)} (\sin\omega t - \xi\cos\omega t) e^{-\alpha z}, \tag{10}$$

where $$\xi = k\alpha^2/\omega = (\delta\alpha)^2/2. \tag{11}$$

The interest here is in a solution for which the heat flux at the slab surface z=0 vanishes at all times. This is the case when the skin surface is not in conductive thermal contact with the surroundings, and thermal radiation from the skin surface is neglected; note however, that part of the incident radiative power may be reflected from the skin surface. The solution of Eqs. (8) and (9), subject to the boundary condition $\partial T/\partial z = 0$ at z=0, is $$T = \frac{\alpha P}{c\rho\omega \sqrt{(1+\xi^2)}} \left\{ \sin(\omega t - \psi) + \frac{1}{\sqrt{2}} \sin(\omega t - z/\delta - \phi) \right\} e^{-z/\delta}, \tag{12}$$

where the angles $\psi$ and $\phi$ are taken in the first or fourth quadrant such that $$\tan \psi = \xi, \ \tan \phi = (1+\xi)/(1-\xi). \tag{13}$$

The amplitude T* of the temperature oscillation T described by Eq. (12) is easily found to be $$T^*(z, \omega) = \tag{14}$$

$$\frac{\alpha P^*}{c\rho\omega \sqrt{(1+\xi^2)}} e^{-z/\delta} \sqrt{\left\{ 3/2 - \sqrt{2\cos\left(\frac{z}{\delta} + \phi - \psi\right)} \right\}}.$$

For varying z, the square root in Eq. (14) oscillates between the values 0.293 and 1.707, due to partial destructive and constructive interference of temperature waves diffusing to the receptors directly from the sites of heat deposit and indirectly via a reflection off the outer skin surface. As a consequence, the spectral filtering exhibited by (14) can actually increase the relative intensity of some harmonics in the receptor temperature waveform as compared with the applied radiative flux waveform. An upper bound for the receptor oscillation temperature amplitude can easily be found from Eq. (14), as $$T^*(z, \omega) \leq \frac{\alpha P^*}{c\rho\omega} \sqrt{(3/2 + \sqrt{2})} \ . \tag{15}$$

If the effective photon absorption length $1/\alpha$ is much larger than the diffusion length $\delta$, then the parameter $\xi$ of (11) is small compared to unity, so that $\psi=0$ and $\phi=\pi/4$ in good approximation, and Eq. (14) becomes $$T^*(z, \omega) = (\alpha P^*/c\rho\omega) e^{-z/\delta} \sqrt{\{3/2 - \sqrt{2\cos(z/\delta + \pi/4)}\}} \ . \tag{16}$$

This expression may then be used for the device of FIG. 2, for the purpose of calculating keying wave shapes which give a prescribed harmonic content of the temperature wave shape at cutaneous thermoreceptors, such as to evoke certain autonomic or cortical responses. For covert operations, harsh sensations may be desired or avoided, depending on the type of operation intended. As an aside it is noted that for certain laser photon frequencies non-thermal interactions with the nervous system might occur, in which photons directly induce in certain cutaneous receptors conformational transitions that cause frequency modulation of spontaneous spiking.

Eq. (16) can also be used for heat pulse induction by microwaves, by taking the absorption length $1/\alpha$ as the skin depth [6] in human tissue.

Delivery of a thermal flux with uniform density can be done by a sheet-type resistor consisting, for instance, of an electrically conducting polymer. If the heat is generated by resistance wires, the delivered heat flux is nonuniform over the heat patch, and an additional calculation is needed for determining the spatial nonuniformity of the temperature variation at the depth of the thermoreceptors. Although tedious, such a calculation is straightforward for the case that the resistance wires are laid out in a periodic pattern such as in the heat patch 3 of FIG. 3. For a thin plane patch with embedded resistor wires in a plane P of constant z, separate solutions can be written down for the two-dimensional diffusion equation in the region between plane P and the free patch surface, in the region between plane P and the skin surface, and in the skin modeled as a homogeneous semi-infinite slab. These solutions are cosine series in the direction y of the wire periodicity, with coefficients that have the essential structure shown in Eq. (1), without the phase shift $\pi/4$, with cosine as well as sine functions, and with both signs for $\delta$. The numerical coefficients in these Fourier series can be determined from the condition $\partial T/\partial z=0$ on the free surface of the heat patch (assuming zero heat loss from that surface), a matching of both T and $\partial T/\partial z$ on the interface between patch and skin, and conditions on the plane P, namely a match of T and a jump in $\partial T/\partial z$ to the extent required by the heat input in plane P by the resistance wires. This heat input can be modeled as a spatially periodic set of delta functions, which can be expanded in a cosine series in the sense of generalized functions [7]. The resulting solution in the skin may be used for calculating the y-wise spatial nonuniformity of the cutaneous thermoreceptor temperature oscillation. This nonuniformity causes a spatial nonuniformity of the evoked FM signals over the neuron assembly upon which the receptor afferents project topographically. These FM signals furnish the excitation of the sensory resonance, and the nonuniformity of excitation amplitude over the involved assembly of neural circuits is expected to have physiological consequences. A similar comment applies to the nonuniformity of frequency modulation amplitude due to the nonuniform distribution of the depth of thermoreceptors.

The analysis given above provides all that is needed for calculating the temperature fluctuations of cutaneous thermoreceptors which results from heat pulse induction in the skin with given parameters. Such a calculation is given here for radiative heat pulses from a heat lamp as in FIG. 8, using data shown in FIG. 11. From these data it is seen that the effective radiant power density window for exciting the resonance near 2.4 Hz ranges approximately from 0.8 to 3.0 mW/cm$^2$. The resulting temperature oscillation amplitude of cutaneous cold receptors is calculated, using z=0.16 mm for the average cold receptor depth [5], at a pulse frequency of 2.386 Hz. The average absorption length $1/\alpha$ for photons from the heat lamp is estimated as 0.2 mm, $c\rho$ is taken as 3.7 J/°cm$^3$ [8], and the diffusivity k as 0.0006 cm$^2$/s [5]. The diffusion length $\delta$ is calculated from (2) as 0.009 cm. Since $1/\alpha=0.02$ cm is considerably larger than $\delta=0.009$ cm, Eq. (16) may be used as an approximation, and one finds the result that the effective window for the cold receptor temperature oscillation amplitude T* ranges from $0.2\times10^{-3}$ to $0.8\times10^{-3}$° C.

For the same experimental setup, with pulse frequencies near ½ Hz, and a radiative power density of 0.6 mW/cm$^2$, for which the full array of mentioned autonomic responses is produced, the estimate of the thermoreceptor temperature oscillation amplitude T* goes as follows. For a pulse frequency of 0.5 Hz, Eq. (2) gives $\delta=0.02$ cm. With $1\alpha=0.02$ cm, the approximation (16) cannot be used, and T* must be calculated from Eq. (14). The parameter $\xi$ of Eq. (11) turns out to be 0.5, and the angles computed from Eq. (13) are $\psi=0.46$ radian and $\psi=1.25$ radian. From Eq. (14) one finds T*=0.3×10$^{-3}$° C. for the amplitude of the cold receptor temperature oscillation for this case. It is satisfying to see that this amplitude lies inside the effective window from $0.2\times10^{-3}$ to $0.8\times10^{-3}$° C. calculated above for the cortical sensory resonance near 2.4 Hz. It is noted that both these results apply to the case where a large skin area was exposed to the pulsed heat radiation. In contrast, in the visible laser experiment mentioned earlier, only 1 cm$^2$ of skin was exposed. In this experiment, the large power density of 5 mW/cm$^2$ is perhaps needed because only a small skin area was exposed.

For heat pulse induction by pulsed microwave radiation, Eq. (16) applies, with the photon absorption length $1/\alpha$ taken as the skin depth $$s = \sqrt{\left(\frac{2}{\sigma\mu\omega}\right)}, \quad (17)$$

where $\sigma$ is the electric conductivity of the tissue, $\mu$ the permeabilty ($4\pi\times10^{-7}$ henries/m), and $\omega$ the radian frequency of the microwave radiation. Eq. (16) shows that, for fixed frequency, cases with equal values for $\alpha P^*$ give equal thermoreceptor temperature oscillation amplitudes. This relation can be used for calculating the power density of the pulsed microwave radiation that is needed for effective excitation of sensory resonances, from the observed effective intensity window that extends from 0.8 to 3.0 mW/cm$^2$ for the heat lamp radiation case analyzed above. From the constancy of $\alpha P^*$ one has $$P^*_{mw} = \alpha s P^*_{hl}, \quad (18)$$

where $P^*_{mw}$ and $P^*_{hl}$ are respectively the power density of the microwave radiation and of the heat lamp radiation, $\alpha$ is the average effective absorption coefficient of the heat lamp radiation photons in the skin, and s is the skin depth given by Eq. (17). For 250 GHz microwave radiation, the skin depth is about 1 mm; with $\alpha$ estimated as 50 cm$^{-1}$, as in the forgoing calculation, Eq. (18) gives $$P^*_{mw} = 5P^*_{hl}, \quad (19)$$

so that for 250 GHz microwave radiation the effective intensity window for exciting the cortical sensory resonance near 2.4 Hz extends from 4.0 to 15.0 mW/cm$^2$.

The above calculation was made for cold receptors, because they are much more numerous in human skin. For warmth receptors the responsivity is larger, but there is an opposing effect due to the smaller exponential factor in Eqs. (14) and (16), that results from the larger average depth of the warm receptors.

Heat loss from the skin due to radiation and sweathing has been ignored. The former effect can be accounted for in straightforward manner, but at low frequencies the sweathing response may be complicated by autonomic feedback loops.

The inventor served as the subject in all the experiments mentioned.

The invention is set apart from other therapeutic uses of heat pulse administration by the minute power densities employed, by the low pulse frequencies and also by differences in field of use. The discovery that induction of weak heat pulses in the skin can excite in man the ½ Hz autonomic sensory resonance and several higher-frequency cortical sensory resonances constitutes a novel development in neuroscience that is unexpected and surprising. The peak power densities applied to the skin are less than 10 mW/cm$^2$, except for those cases of pulsed microwave radiation of long wavelengths that have large skin depths at these wavelengths.

The invention also differs from the relaxation machines where pulsing lights are used for stimulating the retina, with the eyelids open or closed. In contrast, pertinent embodiments of present invention use pulsed light for the induction of heat pulses in the skin, utilizing an entirely different pathway to the brain. That the new field of use of pulsing light is effective for relaxation and for influencing the central nervous system of a subject is unexpected and surprising.

The invention is not limited by the embodiments shown in the drawings and described in the description, which are given by way of example and not of limitation, but only in accordance with the scope of the appended claims.

REFERENCES

[1] H. G. Loos, "Method and Apparatus for Modulating Cutaneous Nerves", U.S. Pat. application Ser. No. 08/447394, 1995.
[2] H. G. Loos, "Magnetic Excitation of Sensory Resonances", U.S. Pat. application Ser. No. 08/486918, 1995
[3] E. R. Kandel, J. H. Schwartz, and T. M. Jessel, *PRINCIPLES OF NEURAL SCIENCE, 3TH EDITION*, ELSEVIER, N.Y., 1991.
[4] Basic Stamp, PARALLAX, INC, Rocklin, Calif. 95765.
[5] H. Hensel, *THERMAL SENSATIONS AND THERMORECEPTORS IN MAN*, Charles C. Thomas, Springfield, Ill., 1982
[6] *AMERICAN INSTITUTE OF PHYSICS HANDBOOK*, D. E. Gray, Ed., McGraw-Hill, N.Y., 1957.
[7] M. J. Lighthill, *FOURIER ANALYSIS AND GENERALIZED FUNCTIONS*, Chapter 5, Eq. (43), Cambridge University Press, 1970.
[8] J. Van Bladel, "The Nature of Electromagnetic Stimuli", in *ELECTRODYNAMIC FIELDS AND NEUROBEHAVIORAL FUNCTION*, Eds. M. E. O'Connor and R. H. Lovely, Allan R. Liss, Inc, New York, 1988
[9] H. Sclichting, *BOUNDARY-LAYER THEORY*, McGraw-Hill, N.Y. 1968.

I claim:

1. Apparatus for exciting in a subject a sensory resonance, the sensory resonance having a resonance frequency, the apparatus comprising:

generator means for generating voltage pulses with a pulse frequency in the range 0.1 to 45 Hz;

heat inducing means, connected to the generator means, for inducing in the skin of the subject heat pulses with an intensity less than 10 mW/cm$^2$, and a frequency equal to the pulse frequency; and tuner means for tuning the pulse frequency to the resonance frequency.

2. Apparatus according to claim 1, wherein the heat inducing means comprise:

resistor means for producing heat; and thermal conduction means for partially conducting the produced heat to the subject when the conduction means are in thermal contact with the skin of the subject.

3. Apparatus according to claim 2, wherein the generator means, resistor means, and the thermal conduction means are confined to a single enclosure.

4. Apparatus according to claim 1, wherein the heat inducing means comprise radiator means for delivering radiative electromagnetic power to the skin of the subject.

5. Apparatus for exciting in a subject a sensory resonance, the sensory resonance having a resonance frequency, the apparatus comprising:

radiation means for producing at the subject a beam of electromagnetic radiation with an intensity less than 10 mW/cm$^2$;

chopping means for modulating said beam, the chopping means having a chopping frequency in the range 0.1 to 45 Hz; and tuner means for tuning the chopping frequency to the resonance frequency.

6. Apparatus according to claim 1, wherein the heat inducing means comprise:

electric blower means for producing an air jet; and electric heater means for heating the air jet.

7. A method for influencing the central nervous system of a subject, comprising the steps of:

inducing in the skin of the subject heat pulses with a dominant frequency in the range 0.1 to 45 Hz and a peak intensity less than 10 mW/cm$^2$; and selecting a value for the dominant frequency appropriate for excitation of a sensory resonance.

8. The method according to claim 7, wherein the inducing comprises applying heat to the skin of the subject by conduction.

9. The method according to claim 7, wherein the inducing comprises applying electromagnetic radiation to the skin of the subject.

10. The method according to claim 7, wherein the inducing comprises applying heat to the skin of the subject convectively.

11. The method according to claim 7, wherein the inducing is initiated by the subject at the time that the need for said influencing is perceived.

12. Apparatus for exciting in a subject a sensory resonance, the sensory resonance having a resonance frequency, the apparatus comprising:

generator means for generating voltage pulses with a pulse frequency in the range 0.1 to 45 Hz;

microwave means, connected to the generator means, for producing microwave radiation pulses with a frequency equal to the pulse frequency; and tuner means for tuning the pulse frequency to the resonance frequency.

* * * * *